(12) United States Patent
Park et al.

(10) Patent No.: US 9,604,370 B2
(45) Date of Patent: Mar. 28, 2017

(54) LINK UNIT, ARM MODULE, AND SURGICAL APPARATUS INCLUDING THE SAME

(71) Applicant: SAMSUNG ELECTRONICS CO., LTD., Suwon-si (KR)

(72) Inventors: Heum Yong Park, Suwon-si (KR); Yong Jae Kim, Seoul (KR); Jeong Hun Kim, Hwaseong-si (KR); Youn Baek Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 590 days.

(21) Appl. No.: 13/759,506

(22) Filed: Feb. 5, 2013

(65) Prior Publication Data
US 2013/0199327 A1  Aug. 8, 2013

(30) Foreign Application Priority Data
Feb. 6, 2012 (KR) .................. 10-2012-0011893

(51) Int. Cl.
*B25J 18/06* (2006.01)
*F16C 11/04* (2006.01)
(Continued)

(52) U.S. Cl.
CPC ............ *B25J 18/06* (2013.01); *A61B 1/0055* (2013.01); *A61B 1/00078* (2013.01);
(Continued)

(58) Field of Classification Search
CPC . B25J 18/06; B25J 19/06; B25J 19/065; B25J 19/104; A61B 1/00078;
(Continued)

(56) References Cited

U.S. PATENT DOCUMENTS 3,858,578 A * 1/1975 Milo ................... A61B 17/02
600/229
4,393,728 A   7/1983 Larson et al.
(Continued)

FOREIGN PATENT DOCUMENTS

CN   1678937 A   10/2005
CN   1690836     11/2005

OTHER PUBLICATIONS

Chinese Office Action dated Jan. 28, 2016, issued in Chinese Application No. 201310048390.5.
(Continued)

*Primary Examiner* — William Kelleher
*Assistant Examiner* — Jude Agendia
(74) *Attorney, Agent, or Firm* — Harness, Dickey & Pierce, P.L.C.

(57) ABSTRACT

A surgical apparatus having sufficient rigidity in a fixed mode and being freely operable in a steering mode includes one or more arm modules having at least one degree of freedom, each arm module including at least one steering cable to steer the arm module and a plurality of link units to form the at least one arm module, each link unit including a head disposed at an upper portion thereof and having a hemispherical shape, a seat formed at a lower portion thereof, and a sliding ball arranged at the seat, wherein the link units are arranged such that the head of one of the link units is seated on the seat of the other of the link units, and the head of one of the link units and the seat of the other of the link units are slid with respect to each other by the sliding ball.

23 Claims, 6 Drawing Sheets

(51) Int. Cl.
*A61B 1/005* (2006.01)
*B25J 9/10* (2006.01)
*A61B 1/00* (2006.01)
*A61B 17/115* (2006.01)
*A61B 17/00* (2006.01)
*A61B 90/50* (2016.01)

(52) U.S. Cl.
CPC ............... *B25J 9/104* (2013.01); *F16C 11/04* (2013.01); *A61B 17/115* (2013.01); *A61B 2017/00278* (2013.01); *A61B 2017/00314* (2013.01); *A61B 2017/00327* (2013.01); *A61B 2090/508* (2016.02); *Y10T 74/20323* (2015.01); *Y10T 403/32622* (2015.01)

(58) Field of Classification Search
CPC ............ A61B 1/0055; A61B 2019/266; A61B 2019/268; A61B 17/115; A61B 1/005; F16C 11/04
See application file for complete search history.

(56) References Cited

U.S. PATENT DOCUMENTS

| | | | |
|---|---|---|---|
| 4,494,417 A * | 1/1985 | Larson | B05B 15/061 414/7 |
| 5,813,976 A * | 9/1998 | Filipi | A61B 1/0055 600/102 |
| 6,478,653 B1 * | 11/2002 | Langton | A63H 3/04 446/373 |
| 6,860,668 B2 | 3/2005 | Ibrahim et al. | |
| 7,171,279 B2 * | 1/2007 | Buckingham | A61B 1/0055 318/568.12 |
| 7,410,483 B2 * | 8/2008 | Danitz | A61B 1/0053 600/141 |
| 7,543,518 B2 | 6/2009 | Buckingham et al. | |
| 7,634,874 B2 * | 12/2009 | Lucas | E04H 4/082 52/108 |
| 7,918,080 B2 | 4/2011 | Zubiate et al. | |
| 7,918,945 B2 | 4/2011 | Izawa et al. | |
| 8,298,161 B2 * | 10/2012 | Vargas | A61M 25/00 600/587 |
| 8,460,271 B2 * | 6/2013 | Piskun | A61B 17/3421 604/513 |
| 8,663,096 B2 * | 3/2014 | Viola | A61B 1/0055 128/898 |
| 8,685,022 B2 * | 4/2014 | Lorenz | A61B 17/6416 606/256 |
| 8,758,232 B2 * | 6/2014 | Graham | A61B 5/065 600/142 |
| 8,864,719 B2 * | 10/2014 | Selvitelli | A61M 5/002 401/133 |
| 8,960,622 B2 * | 2/2015 | von Pechmann | 248/288.31 |
| 2003/0158542 A1 * | 8/2003 | Nguyen | A61B 17/0206 606/1 |
| 2005/0107663 A1 * | 5/2005 | Saadat | A61B 1/0055 600/104 |
| 2006/0199999 A1 | 9/2006 | Ikeda et al. | |
| 2007/0261320 A1 | 11/2007 | Lucas | |
| 2009/0072107 A1 * | 3/2009 | Wilson | A61B 19/26 248/279.1 |
| 2010/0152749 A1 * | 6/2010 | von Pechmann | A61B 19/26 606/130 |

OTHER PUBLICATIONS

Second Office Action issued by The State Intellectual Property Office of P.R. China on Sep. 1, 2016 for corresponding CN Application No. 201310048390.5.

* cited by examiner

LINK UNIT, ARM MODULE, AND SURGICAL APPARATUS INCLUDING THE SAME

CROSS-REFERENCE TO RELATED APPLICATIONS

This application claims the benefit of Korean Patent Application No.10-2012-0011893, filed on Feb. 6, 2012 in the Korean Intellectual Property Office, the disclosure of which is incorporated herein by reference.

BACKGROUND

1. Field

One or more embodiments relate to a surgical apparatus that has sufficient rigidity and moves flexibly.

2. Description of the Related Art

In general, to perform an operation in the abdominal cavity, laparotomy in which an incision is made in the abdomen and surgery is performed in the open state is used. However, laparotomy entails severe pain and long recovery time and causes scarring, and thus, research into minimally invasive surgery has been conducted.

Minimally invasive surgery collectively refers to surgical procedures minimizing the size of the incision. As a representative example, there is laparoscopic surgery. Laparoscopic surgery is an operation in which a plurality of small incisions is made in a patient, a gas is filled into the inside of the patient to form an operation space, and a laparoscope and small surgical instruments are inserted through the incisions. Laparoscopic surgery involving forming a plurality of incisions is also referred to as a multiport surgery.

Laparoscopic surgery is advantageous to an open procedure, but still has some of the same problems as the open procedure because formation of a plurality of incisions is needed.

Thus, research into a single-port surgery in which a single incision is made or natural orifice translumenal endoscopic surgery (NOTES) in which no incision is made is being conducted.

NOTES is a process whereby a flexible surgical apparatus is inserted into a natural opening, i.e., the mouth or anus to reach an operation site and surgery is performed by operating a surgical instrument contained in an overtube.

The single-port operation and NOTES require that a surgical instrument pass through the inside or organs of a patient which has curvature and be securely fixed at an operation site and thus be supported. Therefore, research into a method of achieving both flexibility and rigidity has recently been conducted.

SUMMARY

Therefore, one or more embodiments relate to a surgical apparatus having sufficient rigidity in a fixed mode and being freely operable in a steering mode.

The foregoing described problems may be overcome and/or other aspects may be achieved by one or more embodiments of a surgical apparatus including link units being freely operable in a steering mode.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

In accordance with one or more embodiments, a surgical apparatus may include at least one arm module having at least one degree of freedom, wherein the at least one arm module may include at least one steering cable to steer the arm module and a plurality of link units stacked one upon another to form the at least one arm module, wherein each of the link units may include a head disposed at an upper portion thereof and having a hemispherical shape, a seat disposed at a lower portion thereof, and a sliding ball arranged at the seat, wherein adjacent ones of the link units may be arranged such that the head of one of the adjacent link units may be seated on the seat of the other of the adjacent link units, and the head of one of the adjacent link units and the seat of the other of the adjacent link units may be slid with respect to each other by the sliding ball.

The sliding ball may be installed at the seat such that a portion of the sliding ball protrudes from the seat.

The link unit may further include an elastic unit to elastically bias the sliding ball in a direction in which the sliding ball protrudes from the seat.

The link units may have a fixed mode enabling the link units to contact each other and be fixed to thus have a high rigidity and a steering mode enabling the link units to be spaced apart from each other and thus operable.

The head and seat of the adjacent link units may closely contact each other in the fixed mode.

The head of one of the adjacent link units may contact the sliding ball of the other of the adjacent link units and be spaced apart from the seat of the other of the adjacent link units in the steering mode.

The surgical apparatus may further include a mode switching cable enabling the link units to contact each other or be spaced apart from each other according to the fixed mode and the steering mode.

The link unit may further include a center hole at a central portion thereof such that the mode switching cable passes therethrough.

The at least one arm module may include a first arm module and a second arm module.

The first arm module and the second arm module may operate independently.

The first arm module may include at least one first steering cable driving the first arm module, and the second arm module may include at least one second steering cable driving the second arm module.

The link units each may further include edge holes arranged at edge portions thereof along a circumferential direction such that the at least one first steering cable and the at least one second steering cable pass therethrough.

In accordance with one or more embodiments, an arm module may include a plurality of link units stacked one upon another, wherein each of the link units may include a head disposed at an upper portion thereof, a seat disposed at a lower portion thereof and having a shape corresponding to that of the head, and a sliding ball protruding from a surface of the seat or being inserted into the seat, wherein adjacent ones of the link units may be arranged such that the head of one of the adjacent link units may be seated on the seat of the other of the adjacent link units, and the head of one of the adjacent link units and the seat of the other of the adjacent link units may be slid with respect to each other by the sliding ball, and wherein the arm module may have a fixed mode enabling the head and seat of the adjacent link units to contact each other and a steering mode enabling the head of one of the adjacent link units to contact the sliding ball of the other of the adjacent link units to be slid with respect to each other.

The arm module may further include a mode switching cable passing through a central portion of each link unit.

The sliding ball may be inserted into the seat in the fixed mode and protrude from the seat in the steering mode.

Each link unit may further include an elastic unit to elastically bias the sliding ball outwardly from the seat.

In accordance with one or more embodiments, a link unit may include a head having a hemispherical shape, a seat having a shape corresponding to that of the head and an upwardly concave bottom surface, and a sliding ball arranged at a surface of the seat.

The sliding ball may be movable at a position in which a portion of the sliding ball protrudes from the seat and at a position in which the sliding ball is inserted into the seat.

The link unit may further include an elastic unit to elastically bias the sliding ball outwardly from the seat.

The link unit may further include a center hole passing through a central portion of the link unit.

The link unit may further include a plurality of edge holes arranged at edge portions thereof along a circumferential direction to pass through the edge portions.

BRIEF DESCRIPTION OF THE DRAWINGS

These and/or other aspects of the invention will become apparent and more readily appreciated from the following description of embodiments, taken in conjunction with the accompanying drawings of which.

DETAILED DESCRIPTION

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

Figure 1:
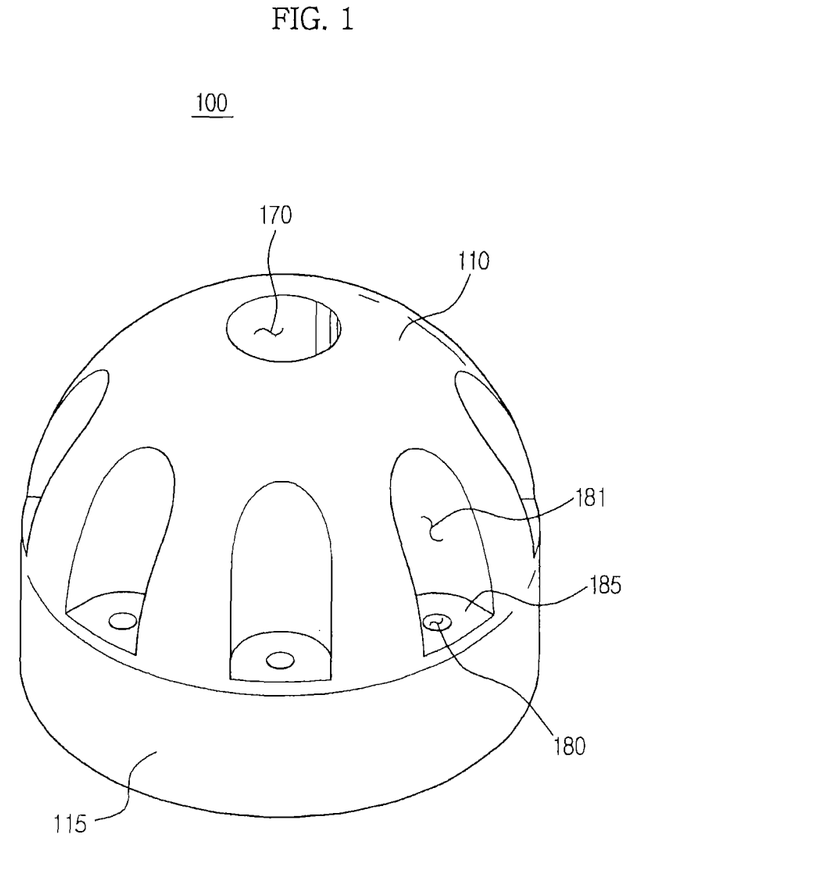
FIG. 1 is a view of a link unit according to one or more embodiments.
Figure 2:
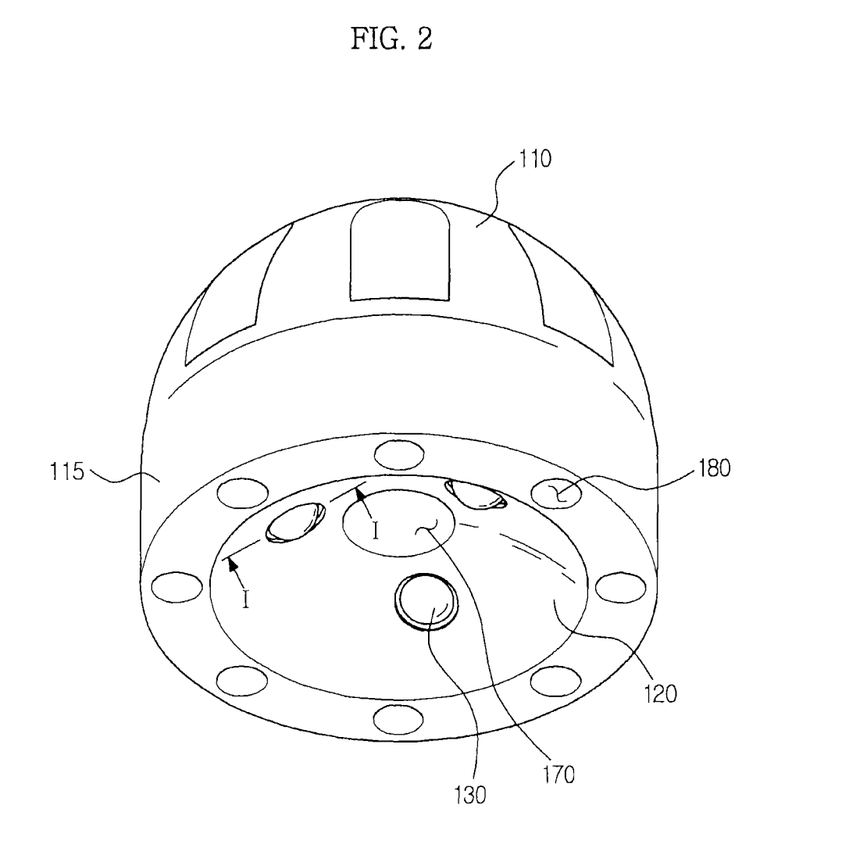
FIG. 2 is a bottom view of a link unit according to one or more embodiments.

FIG. 1 is a view of a link unit 100 according to one or more embodiments. FIG. 2 is a bottom view of a link unit according to one or more embodiments.

As illustrated in FIGS. 1 and 2, the link unit 100 may include a head 110 that has a hemispherical shape and which may be formed at an upper portion of the link unit 100. In addition, the link unit 100 may include a body 115 that is formed below the head 110 and which may have a cylindrical shape.

In FIGS. 1 and 2, it is illustrated that the link unit 100 includes the body 115. In some embodiments, however, the body 115 may not be so formed. For example, the link unit 100 may have an overall hemispherical shape.

A lower surface of the body 115 may be concave to form a seat 120. The seat 120 may have a shape corresponding to that of a head 110 of another link unit 100 having the same shape as that of the link unit 100 so that the head 110 of another link unit 100 may be seated on the seat 120.

The seat 120 may include at least one sliding ball 130 arranged along a circumferential direction so as to protrude from the seat 120. The sliding ball 130 may protrude from the seat 120 so that the sliding ball 130 may be inserted into the seat 120 when external force is applied.

A center hole 170 may be formed at the seat 120 to penetrate a central portion of the link unit 100 so that a mode switching cable 200 (see FIG. 5) may pass through the center hole 170. The center hole 170 may extend from an upper end portion of the head 110 to the seat 120.

Figure 5:
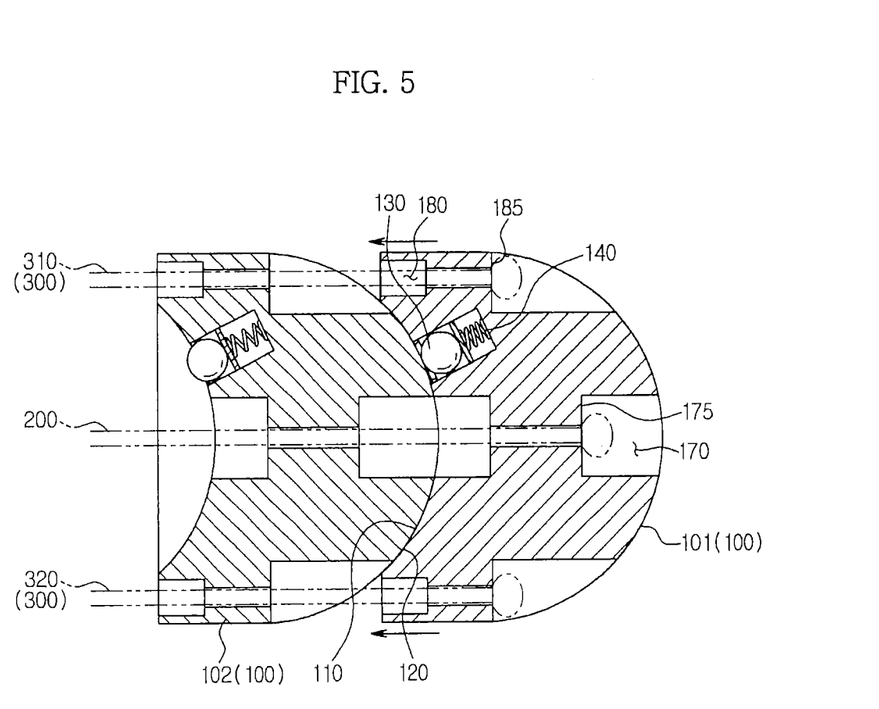
FIG. 5 is a view for explaining an operation of a link unit according to one or more embodiments in a fixed mode.

Referring to FIG. 5, a central engagement step 175 may be formed at the center hole 170 such that an end portion of the mode switching cable 200 may be engaged with the central engagement step 175 to be fixed to the link unit 100.

Edge holes 180 may be formed through edge portions of the link unit 100 so that the steering cables 300 may be disposed through the edge holes 180. That is, the edge holes 180 may be formed through the body 115.

Edge grooves 181 may be formed at portions of the head 110 corresponding to the edge holes 180 such that the steering cables 300 may pass through the edge holes 180.

Portions of an upper surface of the body 115 may be exposed by the edge grooves 181 to form edge engagement steps 185. The edge engagement steps 185 may enable end portions of the respective steering cables 300 to be engaged therewith to be fixed to the link unit 100.

Figure 3:
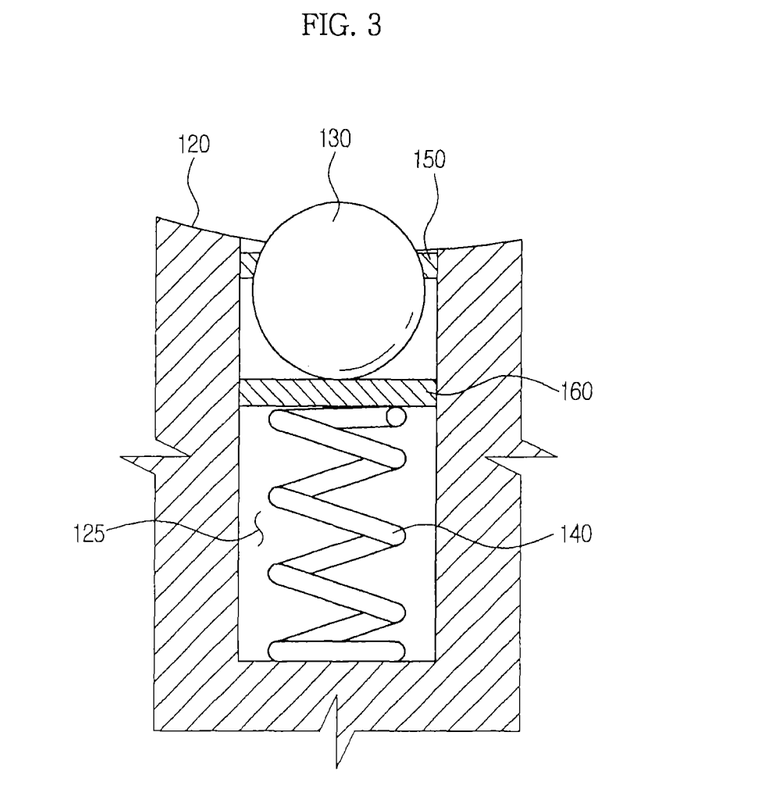
FIG. 3 is a cross-sectional view taken along line I-I of FIG. 2.

FIG. 3 is a cross-sectional view taken along line I-I of FIG. 2.

As illustrated in FIG. 3, a portion of the seat 120 of the link unit 100 may be inwardly recessed to form a ball installation groove 125. With reference to FIG. 2, the number of the sliding balls 130 installed at the seat 120 may be, for example, three, as depicted in FIG. 2, and thus, the number of the ball installation grooves 125 may also be three. Here, the number of the sliding balls 130 may be appropriately adjusted according to one or more embodiments. That is, the number of the ball installation grooves 125 may correspond to the number of the sliding balls 130.

The sliding ball 130 may be inserted into the ball installation groove 125. An elastic unit 140 may be installed inside the ball installation groove 125 such that the sliding ball 130 may be elastically biased outwardly from the seat 120. When external force is not applied by the elastic unit 140 to the sliding ball 130, a portion of the sliding ball 130 may protrude from the seat 120.

A ball plate 160 may be disposed between the elastic unit 140 and the sliding ball 130 so as to connect the sliding ball 130 to the elastic unit 140. The ball plate 160 may be directly connected to the elastic unit 140, and the sliding ball 130 may be mounted on the ball plate 160. Thus, when the ball plate 160 is pushed by the elastic unit 140, the sliding ball 130 may protrude from the seat 120.

To install the sliding ball 130, the ball installation groove 125 may have a larger width than the diameter of the sliding ball 130. An engagement ring 150 having an opening with a smaller diameter than that of the sliding ball 130 may be disposed at an entrance of the ball installation groove 125. Thus, even though the elastic unit 140 presses the sliding ball 130 outwardly from the seat 120, the sliding ball 130 may not completely protrude from the seat 120 by the engagement ring 150 and only a portion of the sliding ball 130 may protrude from the seat 120.

Figure 4:
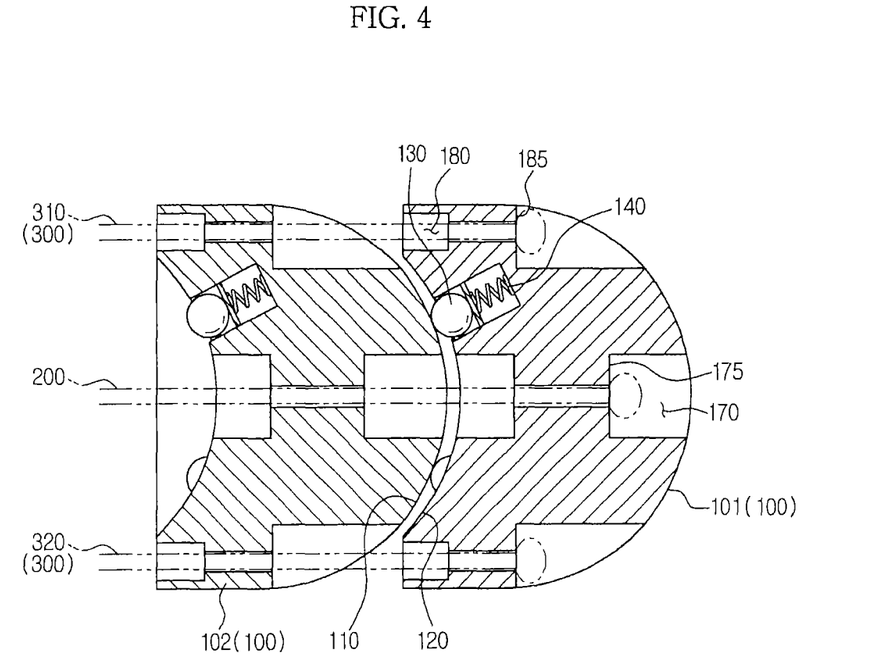
FIG. 4 is a view for explaining an operation of a link unit according to one or more embodiments in a steering mode.

FIG. 4 is a view for explaining an operation of a link unit in a steering mode.

A cross-sectional view of the link unit, which is designated by reference numeral 100, is illustrated in FIG. 4, and thus, an inner structure and coupling structure of the link unit will be first described. Here, an upper side of FIG. 4 is defined as a first direction and a lower side of FIG. 4 is defined as a second direction.

A plurality of the link units 100 as illustrated in FIGS. 1, 2, and 4 may be stacked to form an arm module. In FIG. 4, only two link units of the link units 100 constituting an end portion of the arm module, i.e., a first link unit 101 and a second link unit 102, are illustrated for simplicity.

The first link unit 101 and the second link unit 102 may be sequentially disposed such that the head 110 of the second link unit 102 may be disposed adjacent to the seat 120 of the first link unit 101.

The mode switching cable 200 may be disposed to pass through the center holes 170 of the respective first and second link units 101 and 102. The mode switching cable 200 may have an end portion having a larger diameter than that of the center hole 170, and thus, the end portion of the mode switching cable 200 may be engaged with the central engagement step 175 to be fixed to each of the first and second link units 101 and 102.

The steering cables 300 may be disposed to pass through the edge holes 180 of each of the first and second link units 101 and 102. Each steering cable 300 may also have an end portion having a larger diameter than that of the edge hole 180, and thus, the end portion of the steering cable 300 may be engaged with the edge engagement step 185 to be fixed to each of the first and second link units 101 and 102.

A driving unit (not shown) may be connected to an end portion opposite to the end portion of the steering cable 300 engaged with the edge engagement step 185.

A single link unit may have a plurality of edge holes. In the cross-sectional view of FIG. 4, a pair of edge holes 180 facing each other is illustrated for each link unit. A pair of steering cables 300 is illustrated corresponding to the pair of edge holes 180.

With reference to FIG. 4, the illustrated pair of steering cables 300 includes a first steering cable and a second steering cable, which are designated by reference numerals 310 and 320. The first illustrated steering cable 310 is disposed in the edge hole 180 on the first direction side, and the second illustrated steering cable 320 is disposed in the edge hole 180 on the second direction side.

When the driving unit (not shown) pulls the first steering cable 310 and pushes the second steering cable 320, the first link unit 101 may rotate in the first direction. On the other hand, when the driving unit (not shown) pushes the first steering cable 310 and pulls the second steering cable 320, the first link unit 101 may rotate in the second direction. That is, the first steering cable 310 may be operated correspondingly to operation of the second steering cable 320, whereby the link unit 100 may rotate.

Although the first and second directions indicate two directions, they mean a single degree of freedom on a plane. That is, the first and second steering cables 310 and 320 may enable the link unit 100 to be operated with a single degree of freedom.

Thus, to make the link unit 100 have a degree of freedom of 2, two pairs of steering cables 300 may be needed. Corresponding thereto, two pairs of edge holes 180, i.e., four edge holes, may be needed.

A total number of the edge holes 180 included in the link units 100 according to one or more embodiments may be 8. The number of the edge holes 180 is obtained assuming that two arm modules 10 having a degree of freedom of 2 are formed (see FIG. 6). That is, the number of the edge holes 180 may be adjusted such that each of the arm modules 10 has a degree of freedom of 2.

Figure 6:
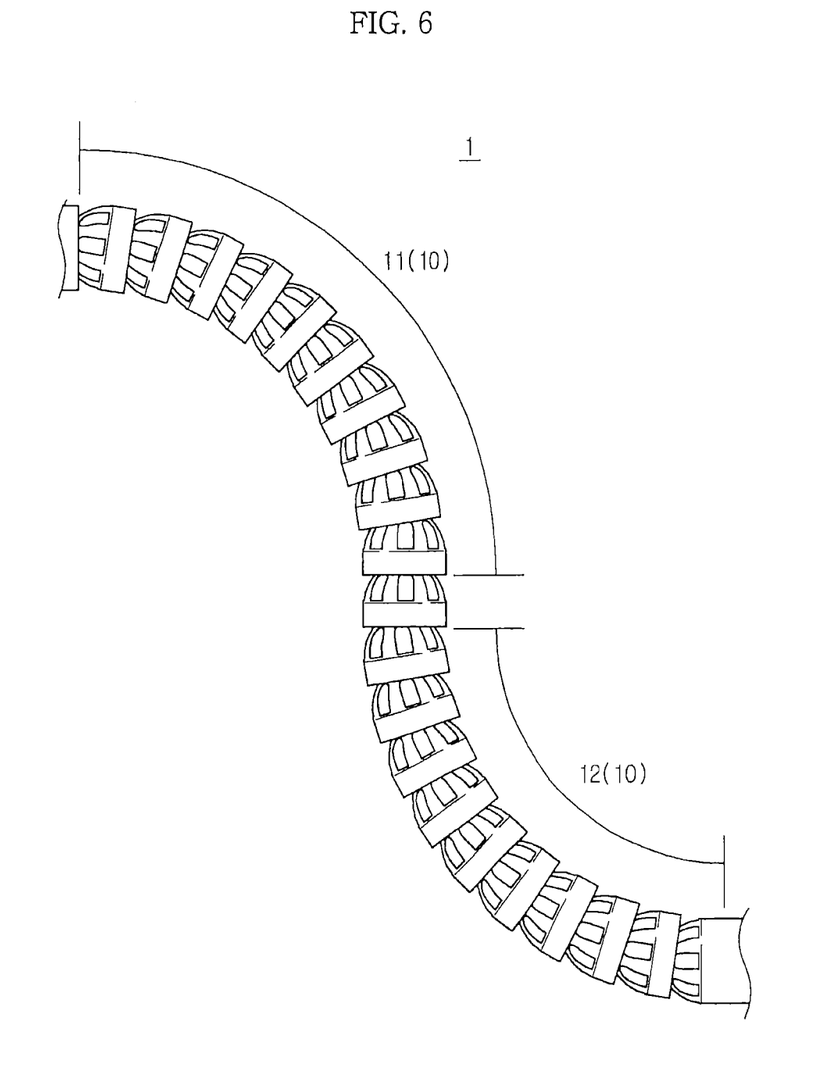
FIG. 6 is a view of a surgical apparatus according to one or more embodiments.

Thus, the number of the edge holes 180 may be increased or decreased to increase or decrease the degree of freedom of the arm module 10, and the number of the steering cables 300 corresponds to the number of the edge holes 180.

Also, the number of the edge holes 180 may be increased or decreased to increase or decrease the number of the arm modules 10 having different degrees of freedom.

Hereinafter, operations of the arm module 10 in a steering mode and a fixed mode will be described.

As illustrated in FIG. 4, the head 110 of the second link unit 102 does not contact the seat 120 of the first link unit 101 and is spaced apart therefrom. The head 110 of the second link unit 102 contacts the sliding balls 130 of the first link unit 101.

In such a configuration, a contact area between the head 110 of the second link unit 102 and the sliding balls 130 of the first link unit 101 may be small, and thus, friction therebetween may be lower than in a case in which the contact area therebetween is large. Accordingly, the first and second link units 101 and 102 may easily rotate with each other.

Furthermore, the sliding ball 130 may be installed to freely rotate in the ball installation groove 125, and thus, the first and second link units 101 and 102 may more freely rotate with the sliding ball 130.

FIG. 5 is a view for explaining an operation of a link unit in a fixed mode.

As illustrated in FIG. 5, when a driving unit (not shown) pulls the mode switching cable 200, the seat 120 of the first link unit 101 and the head 110 of the second link unit 102 may contact each other. The head 110 of the second link unit 102 may press the sliding balls 130 of the first link unit 101, and thus, the sliding balls 130 may be inserted into the first link unit 101.

When the first and second link units 101 and 102 contact each other, friction between the head 110 of the second link unit 102 and the seat 120 of the first link unit 101 may increase. Accordingly, rotation of the first and second link units 101 and 102 may be restricted and the first and second link units 101 and 102 may be securely fixed to each other.

FIG. 6 is a view of a surgical apparatus 1 according to an embodiment.

The arm module 10 including a plurality of link units 100 including the first link unit 101 and the second link unit 102 and a surgical apparatus 1 including the arm module 10 may also exhibit strong rigidity.

The surgical apparatus 1 may include a heavy surgical instrument (not shown) at an end thereof. The surgical instrument is securely fixed in a fixed mode, and thus, operators may be able to implement a surgical operation with perfect posture.

According to one or more embodiments, the head 110 and the seat 120 of the link unit 100 may be surface-treated to maximize frictional force. The surface treatment of the head 110 and the seat 120 may be performed by coating, plating, or heat treatment. However, the surface treatment method is not limited thereto. For example, the head 110 and the seat 120 may be post-treated using other methods to increase frictional force.

Alternatively, the material of the link unit 100 may be modified to increase frictional force. A reason for adopting such a modification is that frictional force varies according to the properties of constituent materials.

When an operator wants to operate the arm module 10 or the surgical apparatus 1 again in such a fixed mode, the operator may drive the driving unit (not shown) to push the mode switching cable 200 so that the link units 100 are separated from each other. Thus, as illustrated in FIG. 4, the head 110 of the second link unit 102 may contact the sliding balls 130 of the first link unit 101, thereby possibly facilitating rotation of the first and second link units 101 and 102.

As illustrated in FIGS. 1, 2, and 6, the surgical apparatus 1 may include two arm modules 10, i.e., a first arm module 11 and a second arm module 12.

In some embodiments, however, the surgical apparatus 1 may include a single arm module or at least three arm modules. When the number of the arm modules 10 increases, the surgical apparatus 1 may be operated flexibly.

The surgical apparatus illustrated in FIG. 6 includes a plurality of the link units 100 illustrated in FIGS. 1 and 2 stacked one upon another. The link units 100 have four pairs of edge holes 180. That is, the arm module 10 includes two pairs of edge holes 180, and thus, the arm module 10 has a degree of freedom of 2. As described above, the degree of freedom may be increased or decreased by changing the number of the edge holes 180.

The first arm module 11 and the second arm module 12 may operate independently. However, the first and second arm modules 11 and 12 may include a single mode switching cable.

The surgical apparatus 1 may include two arm modules 10 operable with an independent degree of freedom in a steering mode and thus may move flexibly and pass along a complex curved path. In a single-port operation or natural orifice translumenal endoscopic surgery, the surgical apparatus 1 may safely insert a surgical instrument into an operation site without damaging, for example, intestines of a patient.

The link units 100 may contact each other and may be securely fixed in a fixed mode and thus may rigidly support the surgical instrument such that the surgical instrument inserted into the surgical site does not escape from the operation site. In addition, even if a heavy surgical instrument is used, the surgical apparatus 1 may endure the weight of the surgical instrument, without bending or deformation.

As is apparent from the above description, a surgical apparatus may have a structure in which a seat of one of adjacent link units and a head of the other of adjacent link units may closely contact each other in a fixed mode and thus may have sufficient rigidity. In a steering mode, on the other hand, the head of the other of adjacent link units and sliding balls of one of adjacent link units may be slid with respect to each other, and thus, the surgical apparatus may operate freely.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A surgical apparatus comprising:
    at least one arm module having at least one degree of freedom, the at least one arm module including,
    at least one steering cable to steer the arm module, and
    a plurality of link units stacked upon one another to form the at least one arm module, each of the link units having an upper portion and a lower portion, and each of the link units including,
        a head disposed at the upper portion, the head configured to have a hemispherical shape,
        a seat at the lower portion, and
        a sliding ball configured to protrude from a groove formed in a surface of the seat, and to translate between a first position and a second position in the groove.

2. The surgical apparatus of claim 1, wherein a portion of the sliding ball protrudes from the seat.

3. The surgical apparatus of claim 1, wherein each of the link units further comprises:
    an elastic unit configured to elastically bias the sliding ball in a direction in which the sliding ball protrudes from the seat.

4. The surgical apparatus of claim 1, wherein
    each of the link units have a fixed mode and a steering mode,
    the fixed mode is configured to enable the link units to contact and be fixed to each other such that a first one of the plurality of link units contacts a second one of the plurality of link units to have a high rigidity, and
    the steering mode is configured to enable the link units to be spaced apart and operable with respect to each other.

5. The surgical apparatus of claim 4, wherein the head of the first one of the plurality of link units and the seat of the second one of the plurality of link units closely contact each other in the fixed mode.

6. The surgical apparatus of claim 4, wherein
    the head of the first one of the plurality of link units contacts the sliding ball of the second one of the plurality of link units adjacent to the first one of the plurality of link units, and
    the head of the first one of the plurality of link units is spaced apart from the seat of the second one of the plurality of link units in the steering mode.

7. The surgical apparatus of claim 4, wherein the surgical apparatus further comprises:
    a mode switching cable configured to enable the first one of the plurality link units to contact the second one of the plurality of link units in the fixed mode or be spaced apart from each other in the steering mode.

8. The surgical apparatus of claim 7, wherein each of the link units further comprises:
    a center hole at a central portion thereof such that the mode switching cable passes there through.

9. The surgical apparatus of claim 1, wherein the at least one arm module comprises:
    a first arm module and a second arm module.

10. The surgical apparatus of claim 9, wherein the first arm module and the second arm module are configured to operate independently.

11. The surgical apparatus of claim 9, wherein
the first arm module includes at least one first steering cable configured to drive the first arm module, and
the second arm module includes at least one second steering cable configured to drive the second arm module.

12. The surgical apparatus of claim 11, wherein each of the plurality of link units comprise:
edge holes at edge portions along a circumferential direction of each of the links, the at least one first steering cable and the at least one second steering cable configured to pass through the edge holes.

13. An arm module comprising:
a plurality of link units stacked upon one another, each of the link units having an upper portion and a lower portion, and each of the link units including,
a head at the upper portion,
a seat at the lower portion, the seat configured to have a shape corresponding to the head, and
a sliding ball configured to protrude from a groove formed in a surface of the seat, and to translate between a first position and a second position in the groove,
wherein the arm module is configured to operate in,
a fixed mode, the fixed mode configured to enable the head of a first one of the plurality of link units and the seat of a second one of the plurality of link units to contact each other, the first link unit and the second like unit being adjacent to each other; and
a steering mode, the steering mode configured to enable the head of the first link units and the sliding ball of the second link units adjacent to the first link unit to contact by sliding with respect to each other.

14. The arm module of claim 13, wherein the arm module further comprises:
a mode switching cable configured to pass through a central portion of each of the link units.

15. The arm module of claim 13, wherein
the sliding ball is inserted into the seat in the fixed mode, and
the sliding ball is configured to protrude from the seat in the steering mode.

16. The arm module of claim 13, wherein each of the link units further comprises:
an elastic unit configured to elastically bias a respective one of the sliding balls outwardly from the seat.

17. A link unit comprising:
a head configured to have a hemispherical shape;
a seat configured to have a shape corresponding to that of the head, the seat further configured to have an upwardly concave bottom surface; and
a sliding ball configured to protrude from a groove formed in a surface of the seat, and to translate between a first position and a second position in the groove.

18. The link unit of claim 17, wherein the sliding ball is configured to move between the first position in which a portion of the sliding ball protrudes from the seat and the second position in which the sliding ball is inserted into the seat.

19. The link unit of claim 18, further comprising:
an elastic unit configured to elastically bias the sliding ball outwardly from the seat.

20. The link unit of claim 17, further comprising:
a center hole passing through a central portion of the link unit.

21. The link unit of claim 17, further comprising:
a plurality of edge holes arranged at edge portions along a circumferential direction of the link unit.

22. A surgical apparatus comprising:
at least one arm module having at least one degree of freedom, the at least one arm module including,
a plurality of link units stacked upon one another to form the at least one arm module, each of the link units having an upper portion and a lower portion, and each of the link units including,
a head having a hemispherical shape, the head being at the upper portion,
a seat on the lower portion, and
a sliding ball configured to protrude from a groove formed in a surface of the seat, and to translate between a first position and a second position in the groove, wherein
the head of one link unit is configured to sit on the seat of an adjacent link unite such that the one link unit and the adjacent link unit rotate with respect to each other.

23. The surgical apparatus of claim 22, wherein each of the of link units have a fixed mode and a steering mode, the fixed mode configured to enable each of the link units to contact and be fixed with each other to have a high rigidity, the steering mode configured to enable each of the link units to be spaced apart and operable with respect to each other.

* * * * *